US012636024B2

(12) United States Patent
    Behnke-Parks et al.

(10) Patent No.: US 12,636,024 B2
(45) Date of Patent: May 26, 2026

(54) SYSTEM AND METHOD FOR COMMINUTION OF BIOMINERALIZATIONS USING MICROBUBBLES

(71) Applicant: AVVIO Medical, Inc., San Francisco, CA (US)

(72) Inventors: William Behnke-Parks, San Francisco, CA (US); David Bell, San Francisco, CA (US)

(73) Assignee: AVVIO Medical, Inc., San Francisco, CA (US)

( * ) Notice: Subject to any disclaimer, the term of this patent is extended or adjusted under 35 U.S.C. 154(b) by 1110 days.

(21) Appl. No.: 16/931,160

(22) Filed: Jul. 16, 2020

(65) Prior Publication Data

US 2021/0015511 A1      Jan. 21, 2021

Related U.S. Application Data

(60) Provisional application No. 62/874,573, filed on Jul. 16, 2019.

(51) Int. Cl.
    *A61B 17/22*      (2006.01)
    *A61N 7/00*       (2006.01)
    *A61N 7/02*       (2006.01)

(52) U.S. Cl.
    CPC .......... *A61B 17/22012* (2013.01); *A61N 7/02* (2013.01); *A61B 2017/22008* (2013.01);
    (Continued)

(58) Field of Classification Search
    CPC ......... A61M 37/0092; A61B 17/22012; A61B 2017/22014; A61B 2017/22025;
    (Continued)

(56) References Cited

U.S. PATENT DOCUMENTS

| | | | | |
|---|---|---|---|---|
| 10,149,906 | B2 * | 12/2018 | Grubbs et al. ... | A61B 17/22022 |
| 2010/0069797 | A1 * | 3/2010 | Cain et al. ........ | A61M 37/0092 |

(Continued)

FOREIGN PATENT DOCUMENTS

| | | | | |
|---|---|---|---|---|
| CA | 2756038 A1 | 9/2010 | | |
| WO | WO2010119363 | * 4/2010 | ............. | A61B 17/22 |

(Continued)

OTHER PUBLICATIONS

Chen, Wen-Shiang et al., "A comparison of the fragmentation thresholds and inertial cavitation does of different ultrasound contrast agents", J. Acoust. Soc. Am., 2003, pp. 643-651, vol. 113, Acoustical Society of America.

(Continued)

*Primary Examiner* — Michael J Tsai
*Assistant Examiner* — Kathleen Paige Farrell
(74) *Attorney, Agent, or Firm* — Intrinsic Law Corp.

(57)      ABSTRACT

A system and method for ultrasound treatment is presented. The system and method alternatingly provide microbubbles in a target region containing a biomineralization, then insonate the microbubbles using an external ultrasound source. The microbubbles cavitate in the target region, destructively affecting the biomineralization and potentially breaking it or reducing its mass over time as a result of the cavitation action. Spatial orientation or alignment of the external ultrasound source may be achieved for best results using acoustic signatures and spectral representations of the same.

8 Claims, 8 Drawing Sheets

(52) U.S. Cl.
CPC ............... *A61B 2017/22014* (2013.01); *A61B 2017/22025* (2013.01); *A61B 2562/0204* (2013.01); *A61N 2007/0004* (2013.01); *A61N 2007/0039* (2013.01)

(58) Field of Classification Search
CPC ............ A61B 17/225; A61B 17/22004; A61B 2017/22008; A61B 8/481; A61B 2017/22007; A61B 2090/378; A61B 2017/00106; A61B 2562/0204; A61B 17/22; A61B 17/22029; A61B 2017/22084; A61N 7/02; A61N 2007/0004; A61N 2007/0039; A61N 7/00; A61N 2007/0086; A61N 2007/0056; A61N 2007/0078; A61N 2007/0052; A61N 2007/0073; A61N 2007/0082
See application file for complete search history.

(56) References Cited

U.S. PATENT DOCUMENTS

| | | | |
|---|---|---|---|
| 2019/0175954 A1* | 6/2019 | Levy et al. .............. | A61N 7/00 |
| 2020/0164194 A1* | 5/2020 | Leighton et al. . | A61M 37/0092 |
| 2021/0170204 A1* | 6/2021 | Vortman et al. .. | A61M 37/0092 |

FOREIGN PATENT DOCUMENTS

| | | | | |
|---|---|---|---|---|
| WO | 2010119363 A1 | 10/2010 | | |
| WO | WO2016151595 | * 3/2016 | ......... | A61B 17/2202 |
| WO | 2016151595 A1 | 9/2016 | | |

OTHER PUBLICATIONS

ISA, "International Search Report", PCT/US20/42337, Oct. 9, 2020.

* cited by examiner

SYSTEM AND METHOD FOR COMMINUTION OF BIOMINERALIZATIONS USING MICROBUBBLES

RELATED APPLICATIONS

The present application claims the benefit of and priority to Provisional Application Ser. No. 62/874,573, entitled "Method and device for microbubble placement and insonation for the erosion, displacement and/or fragmentation of biomineralizations" filed on Jul. 16, 2019, which is hereby incorporated by reference.

TECHNICAL FIELD

This invention relates generally to treatment of harmful biomineralizations using gas bubbles which are excited or cavitiated using ultrasound energy so as to cause damage to the structure of said biomineralizations.

BACKGROUND

Biomineralizations such as kidney and urinary stones are a health problem with several conventional treatment methods and treatment systems. Each conventional treatment method and system has disadvantages, some or all of which are overcome by the present systems and methods.

The prior art has recognized the use of small gas bubbles in proximity to biomineralizations as a means for comminution of stones and similar unwanted objects through high intensity acoustic action on said gas bubbles and the resulting effects of intense cavitation of said gas bubbles at or near the unwanted biomineralizations. Shock wave lithotripsy employs an external high-intensity acoustic shock wave generator to deposit an intense acoustic shock wave at or near an unwanted biomineralization such as a kidney stone. The shock wave and/or cavitation of gas bubbles exerts destructive forces on the kidney stone causing it to break into pieces that can then be passed by the patient. For example, Grubbs et al (U.S. Pat. No. 10,149,906) and others address potential solutions using targeting microbubbles.

Some art uses the broadband emissions from microbubble clusters to detect bubble dynamics related to the above phenomena. Yet, challenges such as detection and placement and localization of such treatments are imperfect, and harmful side effects are possible on account of collateral damage to healthy tissues surrounding the kidney stone. Similar concerns exist for attempts to treat urinary calculi and other biomineralizations using non-invasive acoustic therapy methods. In some examples, the prior art requires the use of computed tomography, magnetic resonance imaging, or other means in an attempt to detect or localize a treatment region, which introduce expense and complexity and other technical problems overcome by this invention.

The prior art is limited in its capacity to detect, localize and to address the problem of biomineralizations in the body, including some particular aspects surrounding this problem such as localization, attenuation, and timed delivery of insonation during treatment.

SUMMARY

This disclosure describes an approach to the detection, characterization and/or treatment of unwanted biomineralizations. A minimally invasive catheter to introduce small gas bubbles (for example but not limited to engineered microbubbles) in close proximity to biomineralizations, and then insonate them with ultrasound of a given frequency and acoustic pressure. The acoustic and hydro dynamic forces of the incident soundwaves as well as the resulting violent oscillation, vibration and rapid volumetric collapse (e.g., cavitation) of the microbubbles at the surface of or near the biomineralizations is exploited for diagnostic and/or therapeutic effect. Specifically, the present disclosure provides one or more embodiments for a method of placement of a plurality of microbubbles at a target site, then exciting or cavitating the microbubbles with an external acoustic source to generate said bubble dynamics or cavitation events, both at an individual bubble level and at the level of the bubble cluster or cloud as a multi-bubble entity. The acoustic emissions from the insonated microbubbles are used to determine indicia for detection of events of interest, which can be then used to determine or guide a treatment, or to monitor said treatment.

The inertial cavitation (IC) activity and signature of the present microbubbles can be used to detect and localize or spatially align the treatment of biomineralizations such as urinary stones where the microbubbles may attach, accumulate or be concentrated.

Successive insonations at various time scales are presented and uniquely exploited by the invention so as to achieve preferred diagnostic and/or therapeutic effects. In some aspects, a treatment can include a macrocycle and a microcycle of acoustic energy applied to the microbubbles mentioned above. The macrocycle describes a series of microbubble placement and insonation events are carried out wherein microbubbles are placed in the target region then insolated with an external ultrasound source. The microcycle describes a sequence of on and off activations of an acoustic (ultrasound) wave by said external ultrasound source so as to create a series of ON- and OFF-times of a given duty cycle. The invention controllably applies said acoustic energy at a target region containing the unwanted biomineralization, and is capable of controlling, monitoring and spatially positioning or aligning the treatment acoustic field of the ultrasound source with respect to the target region or mineralization.

An embodiment is directed to a method comprising determining a target region; alternatingly, in a macrocycle of bubble placement and insonation stages, introducing a plurality of microbubbles into said target region during the bubble placement stage, and insonating the plurality of microbubbles with an external ultrasound source during the insonation stage; wherein the ultrasound source emits ultrasonic energy at selected times during the insonation stage and the ultrasound source does not emit ultrasonic energy during the bubble placement stage.

Another embodiment is directed to a method for controllably causing microbubble cavitation, comprising alternatingly, in a macrocycle of bubble placement and insonation stages, introducing a plurality of microbubbles into said target region during the bubble placement stage, and insonating the plurality of microbubbles with an external ultrasound source during the insonation stage so as to cause inertial cavitation of more than one of the plurality of said microbubbles within said target region; detecting an acoustic emission of said microbubbles undergoing inertial cavitation so as to derive a quantifiable inertial cavitation (IC) signature; and spatially directing said external ultrasound source based on said derived IC signature.

Yet another embodiment is directed to a system for applying ultrasound energy, comprising an ultrasound source configured and arranged to non-invasively deliver ultrasound energy to a target region; a microbubble injector configured and arranged to place a plurality of microbubbles into a target region during a bubble placement time; a controller coupled to said ultrasound source, configured and arranged to alternatingly cause insonation of the target region during an insonation time and to not cause insonation of the target region during said bubble placement time; said controller further configured and arranged, during the insonation time, to alternately activate said ultrasound source during an ON-time of said insonation time and to deactivate said ultrasound source during an OFF-time of said insonation time.

Still another embodiment is directed to a method for non-invasive targeting of biomineralizations, comprising introducing a plurality of chemically-tagged microbubbles into a target region containing a biomineralization so as to accumulate the microbubbles on a surface of said biomineralization; targeting the microbubbles with ultrasound energy to cause inertial cavitation of the microbubbles; and monitoring an acoustic signature of said microbubbles during their cavitation.

BRIEF DESCRIPTION OF THE DRAWINGS

Fora fuller understanding of the nature and advantages of the present concepts, reference is made to the following detailed description of preferred embodiments and in connection with the accompanying drawings in which.

DETAILED DESCRIPTION

A system and method for ultrasound treatment is presented below. The system and method alternatingly provide microbubbles in a target region containing a biomineralization, then insonate the microbubbles using an external ultrasound source. The microbubbles cavitate in the target region, destructively affecting the biomineralization and potentially breaking it or reducing its mass over time as a result of the cavitation action. Spatial orientation or alignment of the external ultrasound source may be achieved for best results using acoustic signatures and spectral representations of the same.

As mentioned, microbubbles such as engineered bubbles are provided at a treatment zone of interest. The treatment zone may be a urinary duct, kidney, bile or other duct or organ where a biomineralization such as a urinary stone has formed. Other targets that may be addressed by this invention include blood clots, fibroids, cancerous tumors or other plaques. The bubbles may comprise stone-surface accumulating (SSA) microbubbles that, while acoustically insonated, facilitate the mechanical erosion and fragmentation of stones for the treatment of urinary stone disease. The microbubbles may be tagged with a chemical tag so as to achieve the present objectives or be more likely to aggregate at or near an unwanted biomineralization such as a kidney stone, urinary stone, etc. In an aspect, the microbubble activity permits desired diagnostic or detection using acoustic sensors such as hydrophones, or other diagnostic imaging means (whether acoustic or radiological).

Mechanical action of the microbubbles is achieved by insonation using an external ultrasound source, producing inertial collapse and pressure focusing against urinary stones. The intensity and center frequency of the applied ultrasound signal, as well as the duty cycle and pattern for activating the ultrasound source are controllable and configured to suit a given application. Monitoring microbubble dynamics and correlating signatures of inertial collapse with treatment parameters presents a strategy for gaining further insights on the mechanism of action as well as intratreatment monitoring for improving clinical outcomes.

Figure 1:
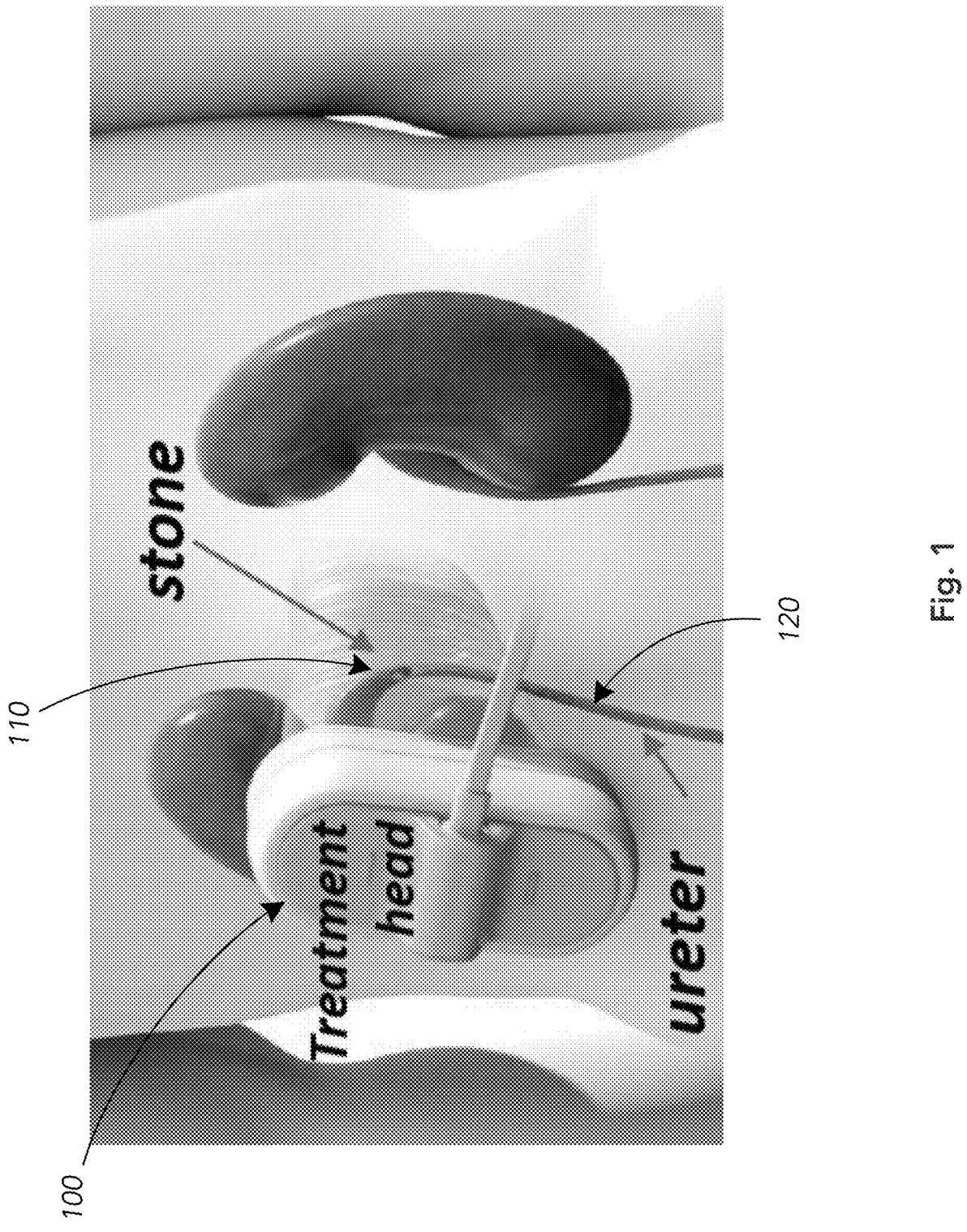
FIG. 1 illustrates a depiction of a target region and treatment device for treating a stone lodged in a ureter or similar anatomy.

FIG. 1 depicts a simplified arrangement of the present ultrasonic treatment device or treatment head 100 comprising one or more ultrasonic transducers which deliver ultrasonic energy to a target region containing an unwanted biomineralization such as a urinary stone 110 lodged in a patient's ureter 120. The ultrasound source is controllable and can be configured and arranged to be activated or deactivated (ON or OFF) so as to temporally modulate the intensity of deposited ultrasound energy at the target region. The ultrasound source may be pulsed or operated with a desired duty cycle, or otherwise programmed to produce desired sequences of ultrasound energy according to a macrocycle and microcycle described herein. In one non-limiting example, the ultrasound source is configured to generate acoustic energy having a center frequency or fundamental being lower than 1 megahertz (MHz), and in a specific non-limiting example a center frequency of about 500 kilohertz (kHz). These frequencies are given by way of example and are not limiting. In an aspect, controlling the generated frequency can optimize the effect of the ultrasound waves on the present microbubbles, causing them to experience large variations in size (effective radius) during operation of the ultrasound, which may enhance the broad band inertial cavitation (IC) signature of the bubbles.

The invention may be used to detect and/or treat conditions related to acute renal colic, which is a potentially debilitating condition caused by an obstruction of the urinary tract. Discrimination of a target (e.g., a bubble-coated biomineralization) from surrounding objects such as bone, is possible because the present invention allows for localization and positioning on account of the directional alignment available between the external acoustic source and the target biomineralization and microbubble formation. Microbubble mediated lithotripsy as described herein may be used to resolve or reduce obstruction of the urinary tract, but the invention is not limited to this application.

In an aspect, microbubbles (including but not limited to engineered microbubbles) are iteratively placed and then insonated by an external acoustic source as part of a macrocycle. The macrocycle may be in some examples comprise a nested microcycle in the insonation period to produce a desired duty ratio. In a non-limiting example, the operation of the system applies the acoustic energy in a given duty cycle or ON-time. The duty cycle is controllable by a processor or controller 230 to achieve almost any desired duty cycle. In a non-limiting example, the duty cycle may be between 1% and 10%, for example 5%. The response of the microbubbles and system can be used to aid the development of an intra-treatment monitoring approach.

Figure 2:
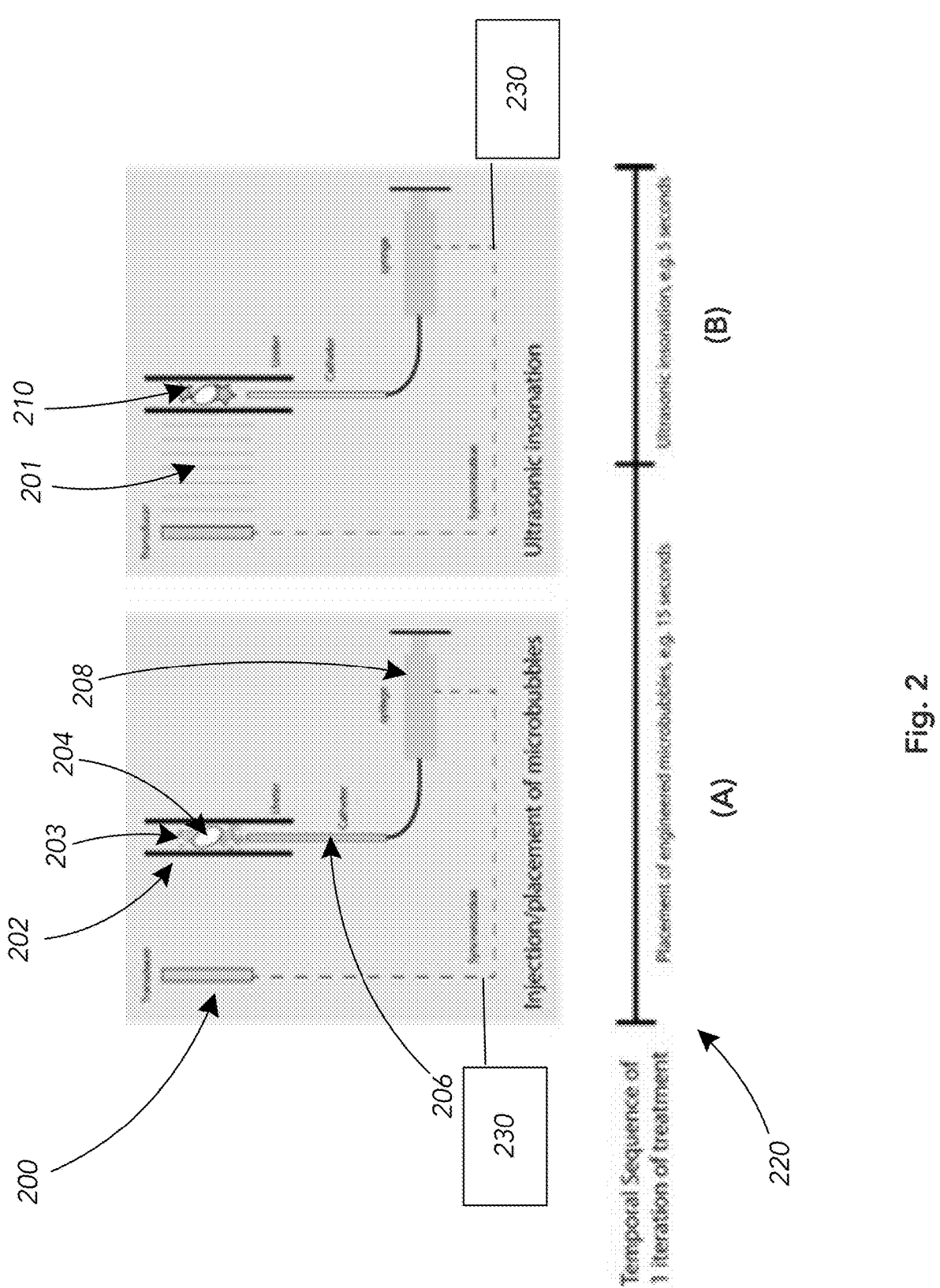
FIG. 2 illustrates an arrangement for placing microbubbles within a target region and for insonating and cavitating said microbubbles.

FIG. 2 illustrates a system and method for placing and insonating the microbubbles in a target region. FIG. 2 (A) depicts placement of engineered microbubbles 203 proximally to an undesired biomineralization (e.g., urinary stone) 204 within a ureter 202. The microbubbles may be injected using a syringe or pump 208 through a catheter 206 as best suits a particular situation. The external acoustic (ultrasound) source 200 is generally inactive (OFF) during the placement of the microbubbles as shown. For example, a processor-controlled circuit or controller 230 may activate and deactivate the ultrasound source 200 at intervals programmed accordingly. In some aspects, the microbubbles 203 will gather or concentrate on or near the stone 204.

FIG. 2(B) depicts the stage of insonation where ultrasound source 200 is activated to deliver a controlled ultrasonic energy waveform 201 to the microbubbles 203 so as to cause inertial cavitation events 210. In this stage the microbubble injection source (syringe or pump 208) is inactive and further microbubbles are not being introduced. During operation, steps (A) and (B) are repeated, alternating the injection of bubbles and application of ultrasound thereto in a programmatical way, defining what is referred to herein as a macrocycle of serial bubble/ultrasound applications until the treatment is complete.

Among other concepts, the present disclosure addresses the change in mass loss of biomineralizations (e.g., stones) and the inertial collapse of the microbubbles measured via passive cavitation detection (PCD) as a function of time and pressure.

Figure 3:
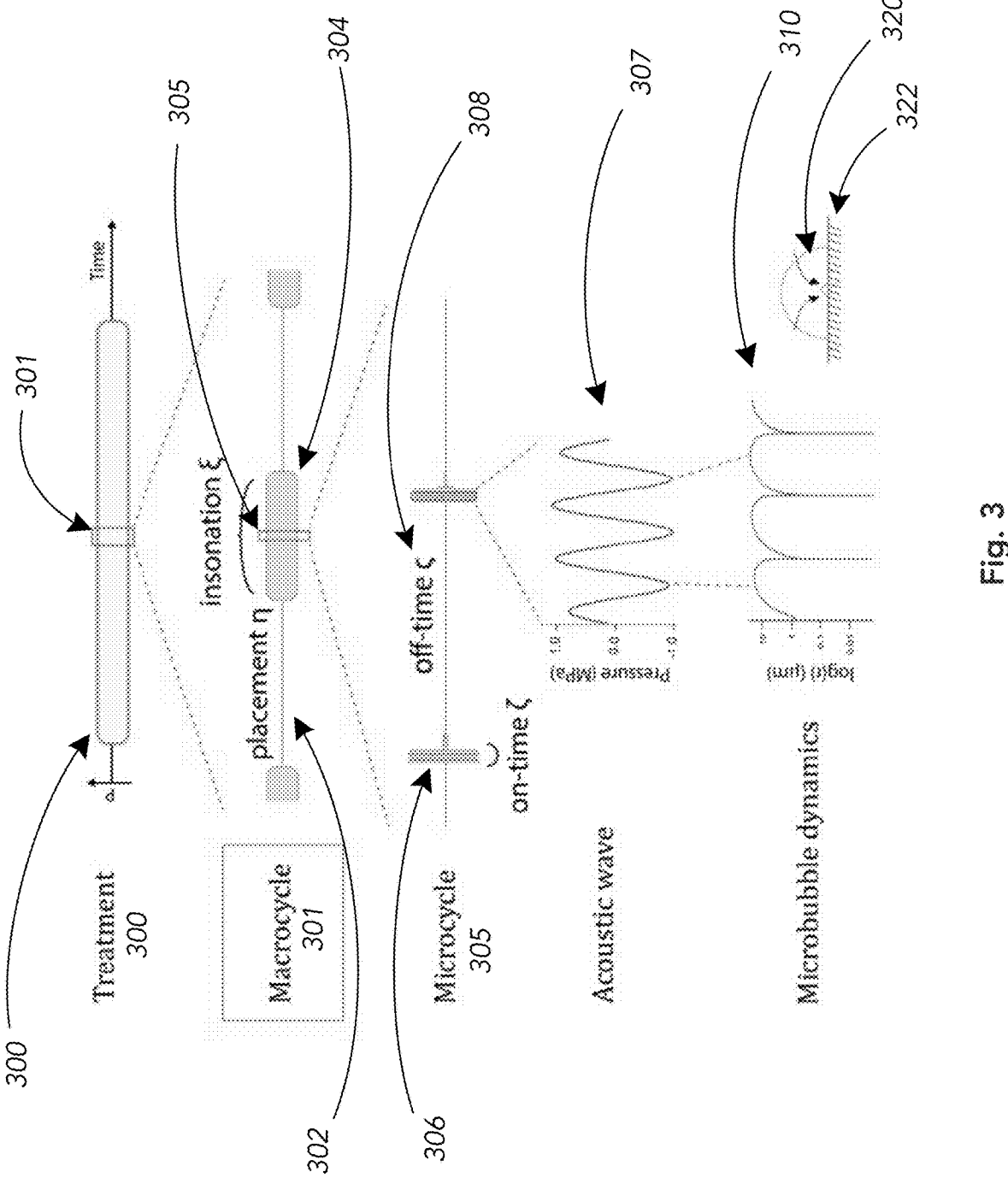
FIG. 3 illustrates a scheme for applying insonations at macrocycles and microcycles and related timed events.

FIG. 3 depicts an exemplary sequence of application of ultrasonic energy to a target region according to the invention. This illustration is merely for the sake of example, and those skilled in the art will appreciate that a variety of similar, equivalent or other examples and sequences are possible and may be used in respective implementations. A treatment 300 is illustrated as extending over a given length of time, generally having a defined start time and an end time. At certain times within the treatment time 300 the ultrasound source described is activated and deactivated (or turned on/off) in a controllable or programmable fashion to achieve the desired results.

Within a treatment 300 we see that a plurality of macrocycles 301 are applied as doses of ultrasonic energy applications which are modulated so that bubble placement times 302 (see, FIG. 2A) alternate with insonation times 304 (see, FIG. 2B). The duration of the bubble placement and insonation times may be equal or may be different in various embodiments without limitation. The ultrasound source is generally inactive or off during the placement times 302 and is active or on at certain times within the insonation phase 304. The placement and insonation phases define said macrocycle 301 and may generally be periodic.

During the insonation phase 304 the system applies many repeated smaller pulses or doses of ultrasound energy to the target region. These on-times 306 and off-times 308 within the microcycle 305 are also controllably programmable as needed for a given implementation, and the ultrasound source is alternately activated (on) or deactivated (off) to accomplish the on/off pattern of energy delivery within the microcycle 305 as shown in this non-limiting example.

The specific pulse sequence of an on-time 306 burst of ultrasound energy is expanded and shown as 307, which in this example is a packet of sinusoidal acoustic pressure waves. Other waveforms can also be employed as would be understood by those skilled in the art, without loss of generality.

For the sake of explanation, FIG. 3 also shows the dynamics of a microbubble subjected to a short burst of ultrasound 307. The bubble radius as a function of time is depicted in 310, which shows the extreme change in bubble size (covering several orders of magnitude) which also results in locally extreme hydrodynamic, acoustic and shock wave behaviors against the surface of the unwanted biomineralization. Such local forces can fragment the biomineralization mass and we discuss below the rate of loss of mass (erosion, breakup) of a stone under the conditions of repeated microcycles 301 and macrocycles 305 during a treatment 300.

In an example, stone erosion and fragmentation with microbubble dynamics is disclosed, the time-dependent rate of mass loss of synthetic stones was sampled in situ with ~0.1 mg resolution while insonated (p<1.4 MPa, f=0.5 MHz) at low-duty cycle (5% duty of 500 µs on-time, 100 Hz P.R.F.) in the presence of SSA microbubbles. The PCD signal was analyzed for broadband emission in the range from 1 to 2 MHz, which has previously been correlated with inertial cavitation (IC).

In some aspects, a time-dependent change in IC on the ~1 second timescale is obtained, consisting of an initial biphasic rise-decay ~500 ms in duration, the amplitude of which showed the expected quadratic dependence on pressure, followed by a long-lived tail. This tail suggests that microbubbles, collectively, can persist through a large number of inertial collapse cycles. The mass loss rate m* is also non-linearly dependent on time, with the target biomineralization mass loss rate for 1 second of insonation showing a 5-fold higher rate (inset) when compared to a linear average mass loss rate for a 30 second insonation (dotted line, inset). It can be seen that a passive cavitation detector (PCD) may be used as a tool for gaining further insights into the underlying mechanism of action as well as intra-treatment monitoring for microbubble-facilitated therapy of urinary stone disease.

The invention may therefore comprise an apparatus as well as a method for the clinical treatment of biomineralizations. In some aspects, an ultrasonic source that is synchronized with a placement of engineered microbubbles via a catheter. A pump or human operator infuses/places the bubbles close to the stone, followed by an insonation period, followed by a flush step that injects fresh water, saline solution or other flushing fluid through the injection system or catheter between macrocycles. In addition to the flushing fluids mentioned, the flushing fluid may be used to alter the cavitation activity, and may comprise a fluid with low dissolved gas or elevated dissolved gas, or a fluid with decreased cavitation nuclei, or any suitable fluid that can suppress or exaggerate cavitation. The process may be iterative, whereby the method can consist of a flush step followed by syringe pump/operator infusion/placement of the engineered bubbles close to the stone, followed by an insonation period. Alternative sequences may omit the flush step or include the flush step on non-sequential iterations.

An exemplary protocol comprises intrinsic parameters and a duration for all three steps: insonation period I, placement period P, flush period F. In one embodiment, a group of 5×10^8 microbubbles placed in proximity to a urinary stone, the flush step is performed every iteration and placement period plus flush period (P+F) is 15 seconds. The insonation has a center frequency of 500 kHz with an on-time of 500 microseconds repeated at 100 Hz pulse repetition rate and the insonation period is I=5 seconds, for an iteration time (I+P+(F/X))=20 seconds. This cycle is repeated 80 to 160 times. The present examples are for the sake of illustration and are not intended to be limiting.

Figure 4:
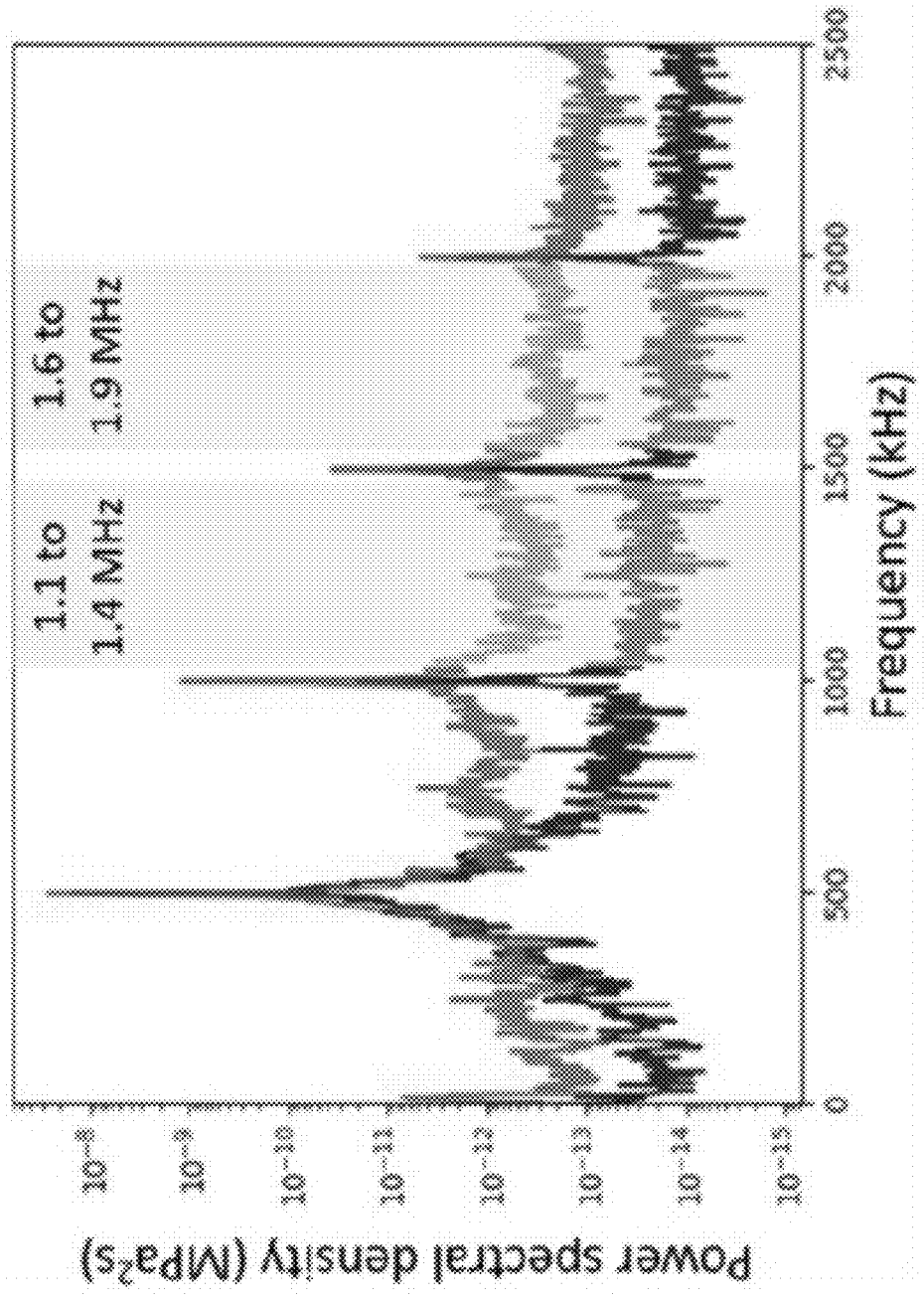
FIG. 4 illustrates a spectral representation of the acoustic emission from said cavitating microbubbles.

FIG. 4 illustrates the power spectral density (PSD) of acoustic signature measured from the excitation and inertial cavitation events in the cluster, cloud or group of a large plurality of microbubbles. A Fourier transform may be applied using the system's processing circuit 230 to the acoustic signature of the cavitation events in the target region, and the resulting spectrum can be plotted, analyzed or processed by human operators or machines in the present system. The power spectral density may employ a fast Fourier transform (FFT) and be computed as $PSD(f)=\Delta t/N|f \cdot FFT(p(t))|^2$ The IC is quantifiable in a number of ways that generally indicate the amount, intensity, or other severity of the cavitation activity in the microbubble and target environment. In one embodiment, the IC is quantified using an integration of the power spectrum over a specified frequency range. In a non-limiting example, the frequency range includes the frequencies above and below a harmonic of the fundamental treatment frequency causing the microbubble cavitation. For example as shown in the figure, if the ultrasound source frequency is centered at 500 kHz (the fundamental) then we may integrate the spectral distribution around the second harmonic (1500 kHz), omitting the frequencies very near to the harmonic itself. In this non-limiting example, the shaded frequency ranges (1.1 MHz to 1.4 MHz and 1.6 MHz to 1.9 MHz) suitably capture a representative range of spectra while excluding the harmonic itself (1.5 MHz) and surrounding harmonics. Any suitable quantification of the amount or intensity or magnitude of inertial cavitation (IC) may be employed as well. Those skilled in the art may devise similar or alternate means of quantifying the inertial cavitation activity caused by the driving ultrasound energy field.

Figure 5:
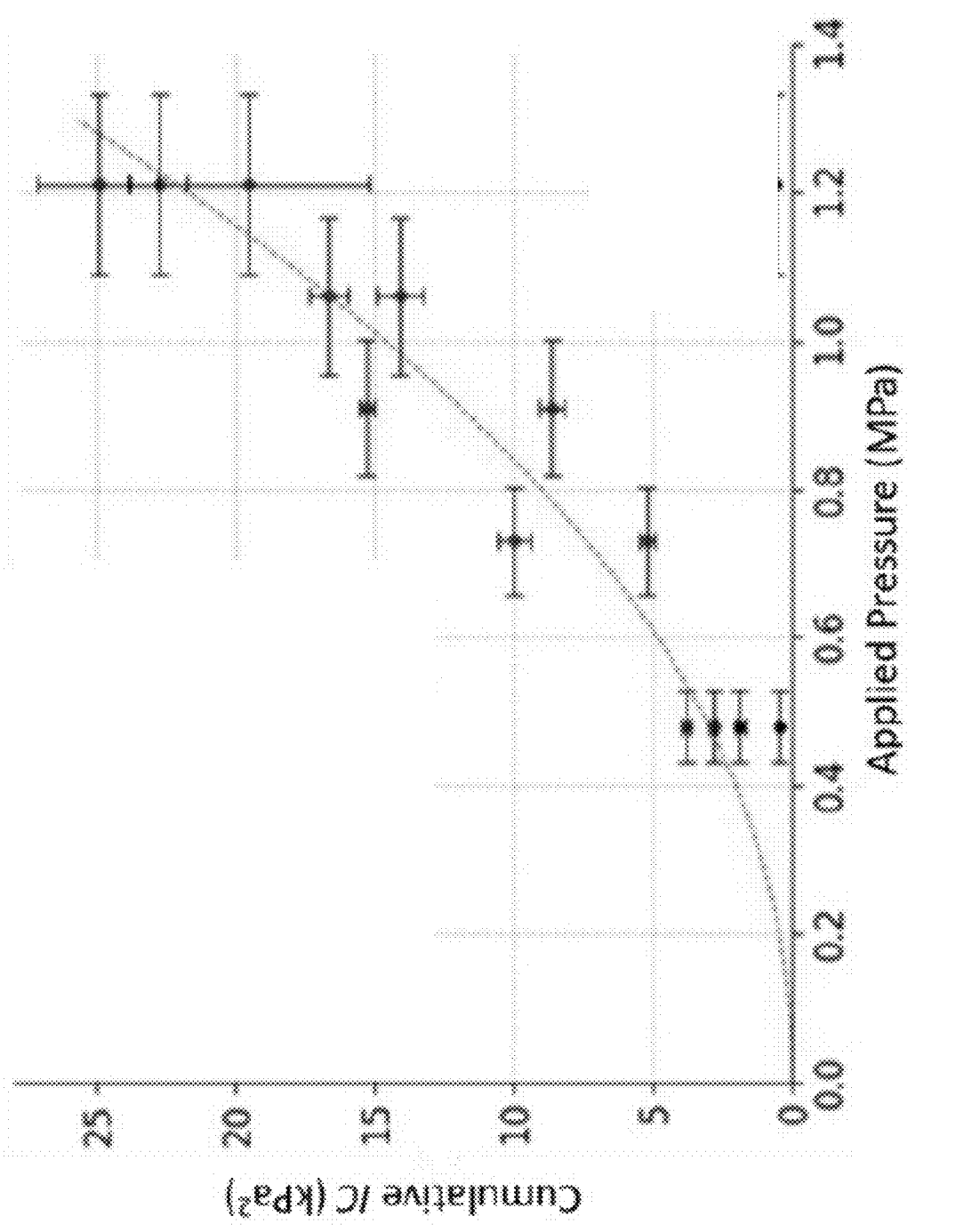
FIG. 5 illustrates an example of the dependence of a quantification of inertial cavitation (IC) as a function of applied acoustic pressure.

FIG. 5 illustrates a general frequency-dependence of cumulative IC (in kilo Pascals squared, kPa^2). The IC measure increases with increasing acoustic pressure amplitude of the applied ultrasound energy.

Figure 6:
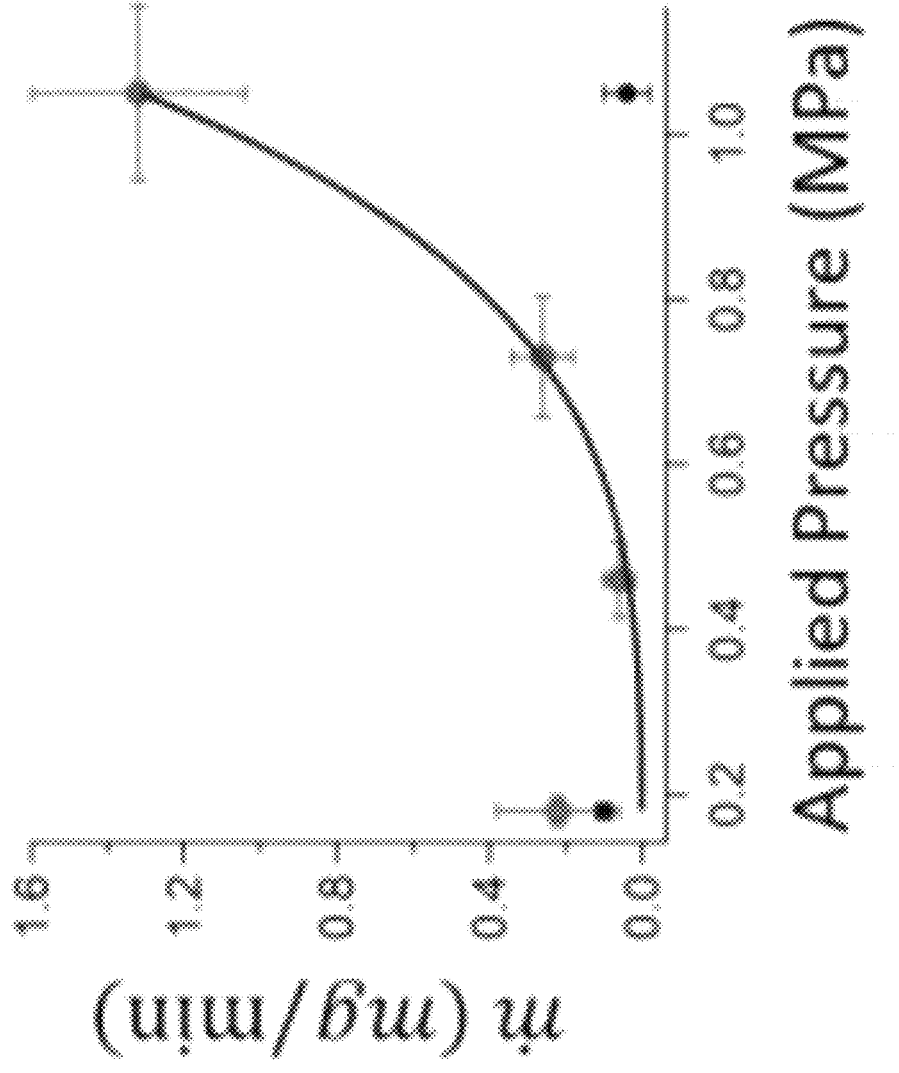
FIG. 6 illustrates an example of the dependence of the rate of mass loss of a biomineralization on applied acoustic pressure.

FIG. 6 illustrates how the rate of decrease of the mass (m) of the biomineralization varies with the increasing acoustic pressure amplitude of the applied ultrasound energy. The rate of loss of mass of the biomineralization (in milligrams per minute, mg/min) increases with increasing ultrasound acoustic pressure applied.

Figure 7:
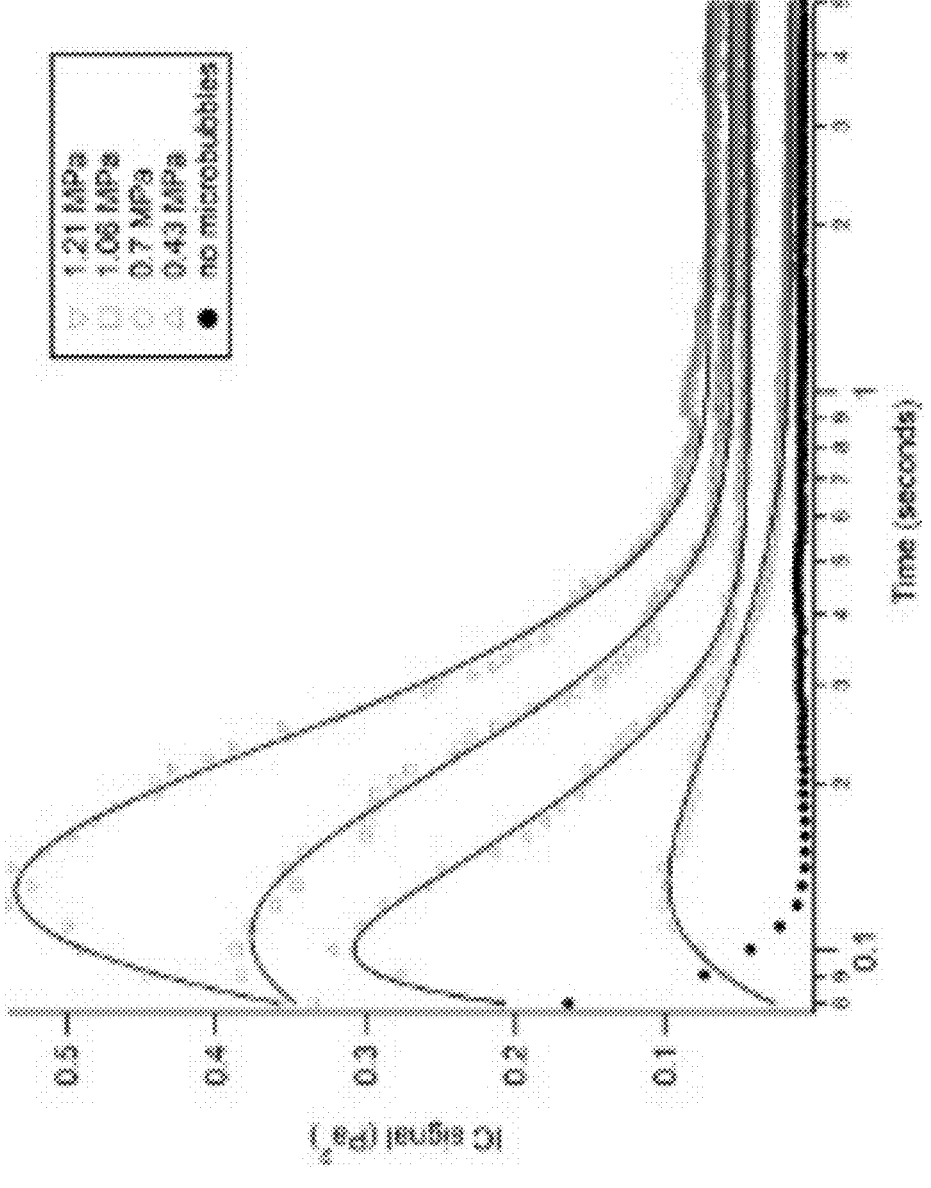
FIG. 7 illustrates exemplary IC signal measurements as a function of time for a variety of exemplary applied acoustic pressures.

FIG. 7 illustrates data supporting the choice of an exemplary insonation period. The data shown here observes a non-linear rate of erosion and inertial cavitation with time. Increasing the amplitude of the acoustic pressure applied to the target region results in a corresponding general increase in cavitation.

Figure 8:
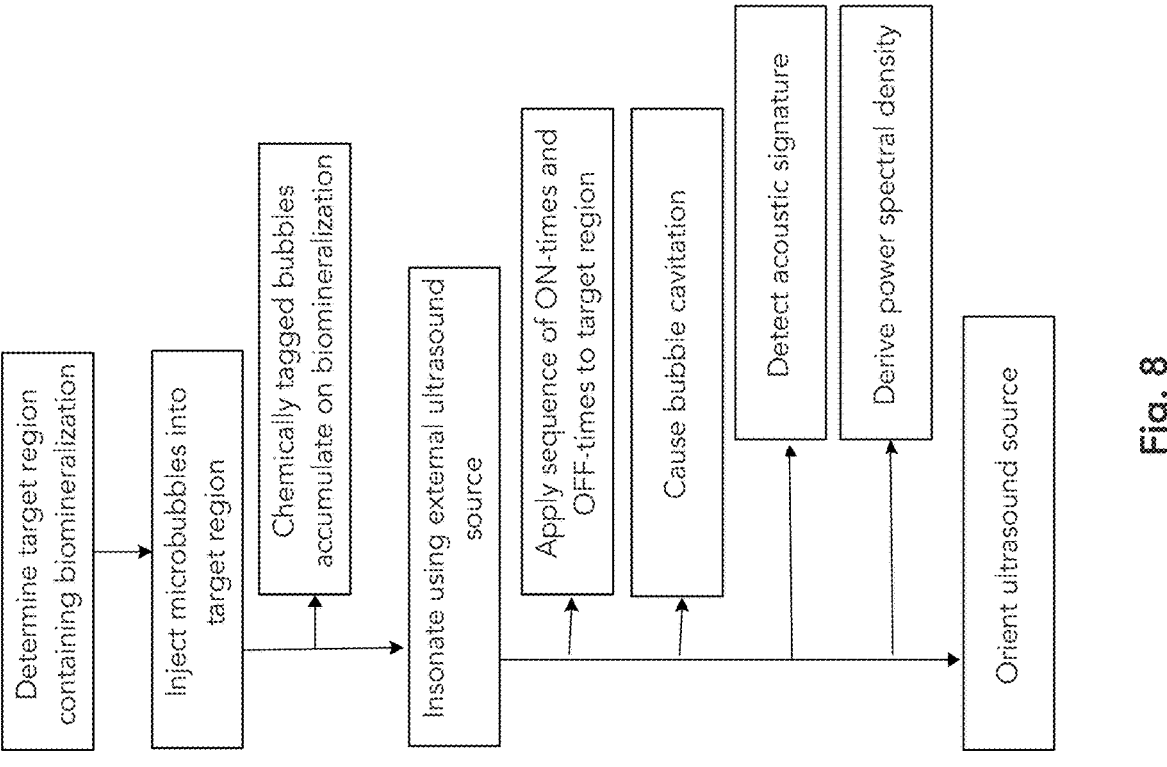
FIG. 8 depicts an exemplary set of steps or acts employed in some embodiments, recognizing that some steps or acts are optional.

FIG. 8 depicts an exemplary set of steps or acts employed in some embodiments, recognizing that some steps or acts are optional.

The present method can be used for intra-treatment monitoring of a patient during treatment and examination of unwanted biomineralizations. In various optional embodiments, the duty cycle of the ON-time to total (ON-time+OFF-time) can be kept to a value under 10% and in some examples a duty cycle of 5% or lower. This may avoid unwanted heating of healthy tissues surrounding the unwanted biomineralization. Those skilled in the art will understand that the relatively low frequencies (e.g., 100 kHz to 750 kHz such as the example above of 500 kHz) are suitable for causing more intense cavitation because keeping below about 1 MHz allows for more extreme bubble size excursions which will result in correspondingly more intense collapse events during cavitation. The selection of a desired driving frequency and driving acoustic pressure causes a corresponding selection of the duty cycle mentioned above, and those skilled in the art will appreciate upon reading this disclosure how to modify the present non-limiting examples to suit their particular needs and implementations.

In another optional aspect, the system may be equipped with both the external ultrasound source (transmitter) as well as a passive cavitation detection and monitoring acoustic sensor (receiver). The acoustic sensor may be integrated into the transmitting ultrasound source as a transducer element in an array of a plurality of elements, or the acoustic sensor may be implemented as a stand-alone sensor such as a hydrophone which is suitably placed with respect to the ultrasound source and target region. Instead of simply detecting reflected ultrasound signals at the source frequency, this invention relies on detection of IC signals arising from the collapse of microbubbles that selectively accumulate near the urinary stone in the ureter. By selectively detecting at broad-band emissions and filtering out harmonics of the input ultrasound frequency, direct reflections from the surrounding bones are discriminated against, providing greatly enhanced detection of the urinary stone.

In yet other optional aspects, the acoustic sensor (or the ultrasound source) may comprise one element, or it may comprise a plurality of phased elements as in an array of transducer elements. In this instance the acoustic sensor array may provide localization and distance or depth information regarding the spatial position of the cavitation events (or biomineralization). Specifically, if the acoustic sensor array is provided as radially concentric elements, it may act as a focusing phased sensor array and provide useful information regarding the depth of the cavitation beneath the patient's skin surface. This can be helpful in treating patients of varying body compositions and sizes and who may have varying fat, muscle or other tissue layers between the patient's skin and the biomineralization.

The time-of-flight constraints of traditional visualization-based imaging can make pattern identification difficult. As an example, consider the case of urinary stones blocking the urinary track at the ureterovesical junction (UVJ). In this case, the distance between the stone and the ilium is small (<1 cm, or between 1 and 2 cm), which is compounded when the trigonometric time-of-flight difference is considered for low-frequency insonation. In addition, the reflection coefficient, which is proportional to the cross-sectional scattering area, for a urinary stone is negligible compared to that of the surrounding ilium, further complicating its detection. The present system and method does not rely on conventional time-of-flight measurement to determine the distance between the acoustic sensor and the target (biomineralization).

In some embodiments, the method comprises dynamically changing a focus (focal depth) of an acoustic sensor array or device. By changing the focus, the amplitude of the IC may be correlated with the stone-to-skin depth. In some embodiments, this skin-to-stone depth can be used to adjust the treatment beam insonation. In some embodiments, the F-number of the hydrophone is smaller than the F-number of the insonating transducer.

In some embodiments, the amplitude of the IC signal is related to the initial size of the biomineralization. In some embodiments, the amplitude of the IC signal is correlated with the degree of fracture.

In some embodiments, intra-treatment monitoring can be correlated with poor treatment outcomes, such as poor transducer-skin coupling, poor bubble placement, etc.

In one variant of the method, the insonating-listening transducer assembly may be translated across the skin. In another variant of the method, the insonating-listening transducer assembly may be pivoted through various angles at the skin surface.

In another variant of the method, the amplitude of the signal can be correlated with the size of the target.

The embodiments and examples provided herein, including the dimensional or quantitative examples are not meant by way of limitation, and those skilled in the art will understand that many other and alternate and equivalent implementations and embodiments are likewise covered by the scope of the following claims.

What is claimed is:

1. A method for causing comminution of a biomineralization, comprising:
   determining a target region in an internal volume that includes a biomineralization having an initial size and mass;
   placing an external ultrasound source on a skin of a subject;
   in a plurality of macrocycles, each macrocycle including a bubble placement stage followed by an insonation stage, introducing a plurality of microbubbles into said target region only during the bubble placement stage, and insonating the plurality of microbubbles with a treatment beam from the external ultrasound source during the insonation stage, the treatment beam delivering energy to said target region to cause inertial cavitation (IC) of at least some of the microbubbles only during the insonation stage, wherein the bubble placement stage and the insonation stage are repeated in an alternating manner during the plurality of macrocycles;
   dynamically changing a focal depth of an acoustic sensor to measure an IC amplitude with respect to the focal depth to determine a depth of the biomineralization with respect to said acoustic sensor;
   dynamically changing a spatial alignment of the external ultrasound source with respect to said biomineralization, by translating or pivoting the external ultrasound source on the skin of the subject, based on the IC amplitude measured by said acoustic sensor;
   dynamically adjusting the treatment beam, including the position and the spatial alignment of said beam, based on the depth and relative position of the biomineralization;
   wherein:
      the ultrasound source emits ultrasonic energy at selected times during the insonation stage,
      the ultrasound source does not emit ultrasonic energy during the bubble placement stage, and
      the microbubbles are not introduced into the target region during the insonation stage;
   and
   using said delivered energy and IC to break said biomineralization into pieces having less size and mass than the initial biomineralization size and mass.

2. The method of claim 1, wherein the external ultrasound source is programmably activated during the insonation stage in a sequence of microcycle ON-times when the external ultrasound source is activated and microcycle OFF-times when the external ultrasound source is deactivated.

3. The method of claim 1, further comprising detecting an acoustic emission of said at least some of the microbubbles undergoing said inertial cavitation so as to derive a quantifiable inertial cavitation (IC) signature.

4. The method of claim 1, wherein insonating the plurality of microbubbles with an external ultrasound source comprises delivering an ultrasound energy beam having a fundamental frequency and having an amplitude sufficient to cause said inertial cavitation of said at least some of the microbubbles.

5. The method of claim 1, wherein the microbubbles comprise engineered microbubbles having a chemical tag.

6. The method of claim 1, wherein said microbubbles comprise stone-surface accumulating (SSA) microbubbles that tend to aggregate at or near said biomineralization.

7. The method of claim 1, wherein said acoustic sensor is integrated into said external ultrasound source as a transducer element therein.

8. The method of claim 1, wherein said acoustic sensor comprises a stand-alone sensor not integrated into said external ultrasound source.

* * * * *